(12) United States Patent
Takada

(10) Patent No.: US 9,522,256 B2
(45) Date of Patent: Dec. 20, 2016

(54) GUIDEWIRE

(71) Applicant: ASAHI INTECC CO., LTD., Nagoya-shi, Aichi (JP)

(72) Inventor: Keigo Takada, Sakai (JP)

(73) Assignee: ASAHI INTECC CO., LTD., Nagoya-shi (JP)

(*) Notice: Subject to any disclaimer, the term of this patent is extended or adjusted under 35 U.S.C. 154(b) by 1 day.

(21) Appl. No.: 14/314,657

(22) Filed: Jun. 25, 2014

(65) Prior Publication Data

US 2015/0088037 A1   Mar. 26, 2015

(30) Foreign Application Priority Data

Sep. 25, 2013   (JP) ................................ 2013-197687

(51) Int. Cl.
*A61M 25/09* (2006.01)

(52) U.S. Cl.
CPC .... *A61M 25/09* (2013.01); *A61M 2025/09083* (2013.01); *A61M 2025/09091* (2013.01); *A61M 2025/09133* (2013.01)

(58) Field of Classification Search
CPC ..................... A61M 25/09; A61M 2025/09133
See application file for complete search history.

(56) References Cited

U.S. PATENT DOCUMENTS

| 5,840,046 | A | 11/1998 | Deem |
| 6,340,441 | B1* | 1/2002 | Meyer ................... A61M 25/09 156/244.12 |
| 7,553,287 | B2 | 6/2009 | Reynolds et al. |
| 8,480,598 | B2 | 7/2013 | Nelson, III et al. |
| 2005/0096567 | A1 | 5/2005 | Reynolds et al. |
| 2006/0047224 | A1 | 3/2006 | Grandfield |
| 2008/0004546 | A1* | 1/2008 | Kato ..................... A61M 25/09 600/585 |
| 2008/0183812 | A1 | 7/2008 | Paul et al. |
| 2011/0245730 | A1 | 10/2011 | Satozaki |
| 2015/0088036 | A1 | 3/2015 | Takada et al. |

FOREIGN PATENT DOCUMENTS

| EP | 0820782 | A2 | 1/1998 |
| EP | 0982046 | A1 | 3/2000 |
| EP | 1 243 283 | A2 | 9/2002 |

(Continued)

OTHER PUBLICATIONS

Aug. 1, 2014 Extended Search Report issued in European Patent Application No. 14173720.5.

(Continued)

*Primary Examiner* — Adam J Eiseman
*Assistant Examiner* — Yasmeen S Warsi
(74) *Attorney, Agent, or Firm* — Oliff PLC

(57) ABSTRACT

In a coil-type guidewire, a coating portion of the coil portion is formed by stacking a plurality of films. An innermost film of the coating portion is arranged to come between adjacent coils of the coil body, and voids are formed between the innermost film and a film disposed outside of the innermost film. By forming such voids, it is possible to easily bend the coating portion and to improve flexibility of the coating portion. As a result, the guidewire in which the coil body is covered with the coating portion and the coil body (the guidewire) can be easily curved.

9 Claims, 5 Drawing Sheets

(56) References Cited

FOREIGN PATENT DOCUMENTS

| EP | 1498152 A1 | 1/2005 |
|---|---|---|
| EP | 1 875 941 A1 | 1/2008 |
| EP | 2371402 A2 | 10/2011 |
| JP | 2007509713 A | 4/2007 |
| JP | 2008011938 A | 1/2008 |
| JP | A-2008-237621 | 10/2008 |
| JP | 2011206494 A | 10/2011 |
| JP | 2016-027923 A | 2/2016 |
| JP | 2016-041349 A | 3/2016 |
| WO | 97/48330 A1 | 12/1997 |
| WO | WO 2004/007014 A1 | 1/2004 |

OTHER PUBLICATIONS

Feb. 26, 2016 Office Action issued in Japanese Patent Application No. 2013-197687.
Feb. 22, 2016 Office Action issued in U.S Appl. No. 14/314,432.
Jan. 7, 2016 Office Action issued in European Patent Application No. 14 173 723.9.
Dec. 17, 2014 Search Report issued in European Application No. 14173724.7.
Oct. 27, 2015 Office Action issued in Japanese Application No. 2013-197685.
Oct. 27, 2015 Office Action issued in Japanese Application No. 2013-197686.
Oct. 27, 2015 Office Action issued in Japanese Application No. 2013-197687.
Aug. 27, 2014 Extended Search Report issued in European Application No. 14173723.9.
Aug. 25, 2015 Office Action issued in U.S. Appl. No. 14/314,432.
Nov. 5, 2015 Office Action issued in U.S. Appl. No. 14/314,473.
Aug. 29, 2014 Partial Search Report issued in European Application No. 14173724.7.
U.S. Appl. No. 14/314,432, filed Jun. 25, 2014.
U.S. Appl. No. 14/314,473, filed Jun. 25, 2014.
May 19, 2016 Office Action issued in U.S. Appl. No. 14/314,473.
Jul. 8, 2016 Office Action issued in Japanese Patent Application No. 2015-229480.
Jul. 8, 2016 Office Action issued in Japanese Patent Application No. 2015-229479.
Jul. 8, 2016 Written Directive issued in Japanese Patent Application No. 2015-229479.
Jul. 8, 2016 Written Directive issued in Japanese Patent Application No. 2015-229480.
Sep. 8, 2016 Office Action Issued in U.S Appl. No. 14/314,473.

\* cited by examiner

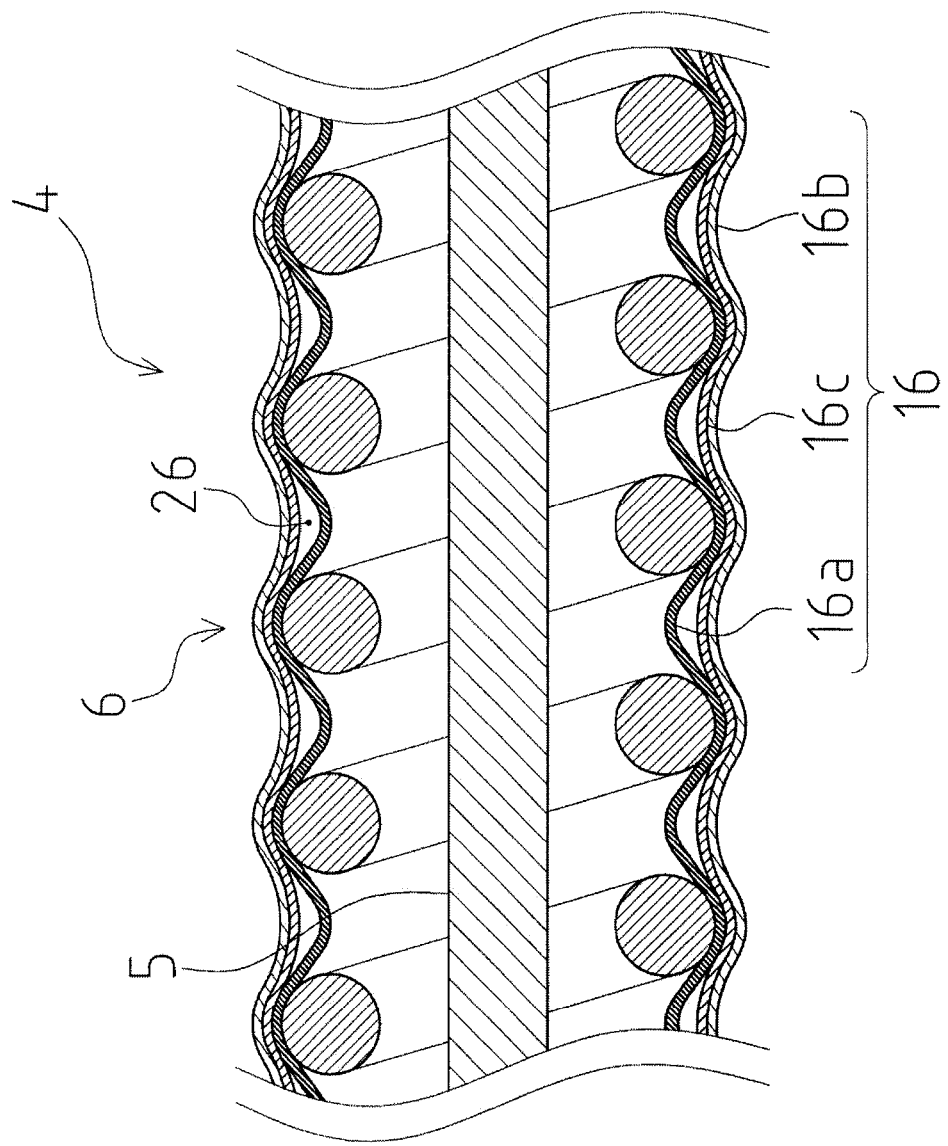

GUIDEWIRE

CROSS-REFERENCE TO RELATED APPLICATION

This application claims priority to Japanese Application No. 2013-197687 which was filed on Sep. 25, 2013, the entire contents of which is hereby incorporated by reference.

BACKGROUND

The disclosed embodiments relate to a medical device. Specifically, the disclosed embodiments relate to a guidewire inserted into a lumen of a blood vessel or the like.

A guidewire used when inserting a catheter into a blood vessel is known. When one wants to insert a catheter, the guidewire is first inserted into a blood vessel and the catheter advances along the guidewire. In this manner, the guidewire functions as a guide for guiding the catheter to a lesion.

As such a guidewire, a guidewire in which a distal end of a core shaft is covered with a coil body (a so-called coil-type guidewire) is generally used. Moreover, a guidewire in which the surface of a coil body is covered with a coating such as a resin for the purpose of securing the ability to slide within the blood vessel is proposed in, for example, U.S. Pat. No. 5,840,046 and Japanese Unexamined Patent Application Publication No. 2008-237621.

SUMMARY

However, in the conventional guidewire described above, since the surface of the coil body is covered with a coating, there is a problem that the coil body (and the guidewire) is difficult to curve or bend.

The disclosed embodiments have been made to solve the above-described problems and aim to provide a technique for enabling a coil body to be easily curved in a guidewire in which the surface of the coil body is covered with a coating.

In order to solve the above-described problems, a guidewire according to aspects of the present invention employs the following configuration. That is, the guidewire includes a core shaft; a coil body that covers the core shaft; and a coating portion that covers the coil body, in which the coating portion is formed by stacking a plurality of films. Portions of an innermost film of the coating portion are arranged to come (protrude) between adjacent coils of the coil body, and voids are formed between the portions of the innermost film that are arranged to come between the wires of the coil body and a film disposed outside of the innermost film.

In such a guidewire, the coating portion is formed by stacking a plurality of films, portions of the innermost film of the coating portion are arranged to come between the adjacent coils of the coil body, and voids are formed between the portions of the innermost film and a film disposed outside of the innermost film. Thus, it is possible to easily bend the coating portion and to improve flexibility of the coating portion. As a result, it is possible to provide the guidewire in which the coil body is covered with the coating portion and the coil body (and the guidewire) can be easily curved.

Moreover, in the guidewire, the coating portion may be formed by stacking at least three films, and voids may be formed between respective films of the coating portion in portions in which the films of the coating portion are arranged to come between the adjacent coils of the coil body.

In such a guidewire, the coating portion is formed by stacking at least three films, and voids are formed between respective films of the coating portion portions in which the films of the coating portion are arranged to come between the adjacent coils of the coil body. Thus, it is possible to improve the bendability and flexibility of the coating portion and to improve the strength of the coating portion. As a result, it is possible to provide a guidewire in which the coil body can be easily curved and the coating portion can resist wear.

Moreover, in the guidewire, the coating portion may be formed such that an outer film is more flexible than an inner film.

When the guidewire (and the coil body) is curved, an outer film of the coating portion is deformed more than an inner film. Thus, since the outer film of the coating portion is more flexible than the inner film, the coil body can be curved more easily. As a result, for example, it is possible to provide a guidewire that can follow the blood vessel satisfactorily even when the guidewire is inserted into a blood vessel that meanders complexly.

BRIEF DESCRIPTION OF DRAWINGS

FIG. 5 is an enlarged view of a coil body and a coating portion of a guidewire according to an exemplary embodiment.

DESCRIPTION OF EMBODIMENTS

Hereinafter, a guidewire according to aspects of the present invention will be described below.

Figure 1:
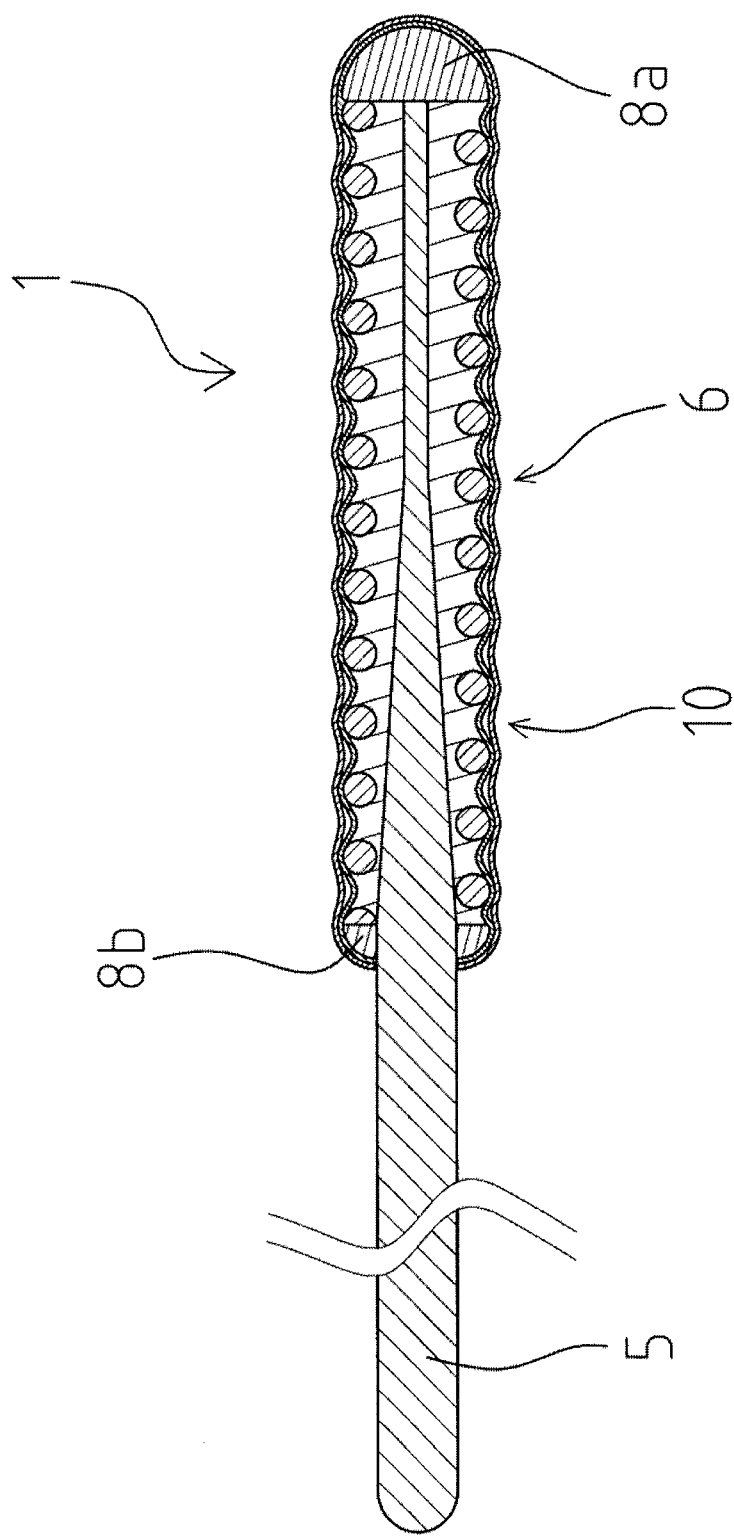
FIG. 1 is a diagram for describing a configuration of a guidewire according to an exemplary embodiment.

FIG. 1 is a diagram for describing a configuration of a guidewire 1. The guidewire 1 includes a core shaft 5, and a coil body 6 that covers the core shaft 5. The core shaft 5 and the coil body 6 are joined together by a junction formed of a solder material or the like. Here, a distal end of the coil body 6 and a distal end of the core shaft 5 are connected by a junction 8a, and a proximal end of the coil body 6 and an intermediate portion of the core shaft 5 are connected by a junction 8b.

Moreover, in the guidewire 1, the surface of the coil body 6 is covered with a coating portion 10. The coating portion 10 is provided to reduce frictional resistance between the surface of the guidewire 1 and the inner wall of a blood vessel to secure slidability when the guidewire 1 is inserted into the blood vessel. Thus, the coating portion 10 is preferably formed of a material (a hydrophilic resin or the like) having small frictional resistance. For example, the coating portion 10 is preferably formed of polyvinyl alcohol, polyvinylpyrrolidone, polyethylene glycol, polyacrylamide, a polyacrylic acid, sodium polyacrylate, poly(2-hydroxyethyl methacrylate), a maleic anhydride-based copolymer, an ethylene vinyl alcohol copolymer, 2-methacryloyloxyethyl phosphorylcholine or the copolymer, a (2-hydroxyethyl methacrylate)-styrene block copolymer, various synthetic polypeptides, collagen, hyaluronic acid, a cellulose-based polymer and mixtures thereof.

Moreover, the coating portion 10 may be formed by adding an additive such as a non-hydrophilic monomer, a cross-linker, a non-volatile solvent, a volatile solvent, or a surfactant to the above-described material.

Figure 2:
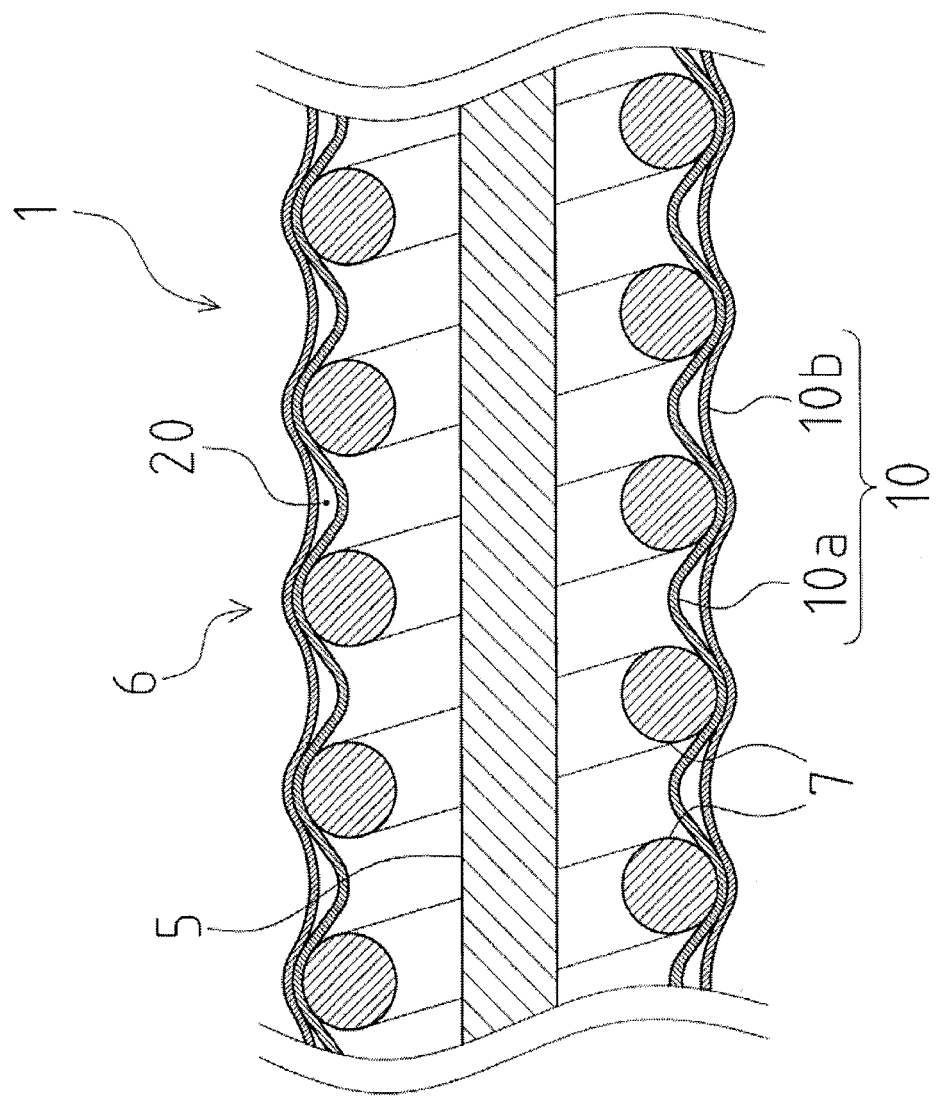
FIG. 2 is an enlarged view of a coil body and a coating portion of the guidewire according to an exemplary embodiment.

FIG. 2 is an enlarged view of the coil body 6 and the coating portion 10 of the guidewire 1. As illustrated in the drawing, the coil body 6 of the guidewire 1 according to the present embodiment is formed in such a shape that adjacent coils 7 are not in contact with each other (a so-called a loose winding).

Moreover, the coating portion 10 on the surface of the coil body 6 is formed by stacking a plurality of films (here, an inner film 10a and an outer film 10b).

In the guidewire 1 portions of the inner film 10a of the coating portion 10 are arranged to come (protrude) between the adjacent coils of the coil body 6, and a void 20 is formed between the portions of the inner film 10a that are arranged to come between the adjacent coils of the coil body 6 and the outer film 10b.

In the guidewire 1, since the void 20 is formed between the portions of the inner film 10a arranged to come between the adjacent coils of the coil body 6 and the outer film 10b, the coating portion 10 is easily bent and is sufficiently flexible.

Conventionally, when the surface of the coil body is covered with the coating portion, the coating portion obstructs the coil body from curving easily when the coil body is curved. As a result, the ability of the guidewire to follow the blood vessel tends to decrease. On the other hand, when the surface of the coil body is not covered with the coating portion, it may be difficult to secure the ability of the guidewire to slide within the blood vessel.

Due to the above reasons, it was conventionally difficult to secure the abilities of the guidewire to slide within the blood vessel and to follow the blood vessel.

In contrast, in the guidewire 1, since the coating portion 10 is easily bent and has excellent flexibility, it is possible to easily bend the coil body 6 while having a configuration in which the coating portion 10 is present on the surface of the coil body 6. As a result, it is possible to secure the abilities of the guidewire 1 to slide within the blood vessel and to follow the blood vessel.

Modifications of the guidewire 1 may be made without departing from the scope of the invention, which are described below. In the following description, the same configurations as those of the guidewire 1 of the first embodiment will be denoted by the same reference numerals, and detailed description thereof will not be provided.

Figure 3:
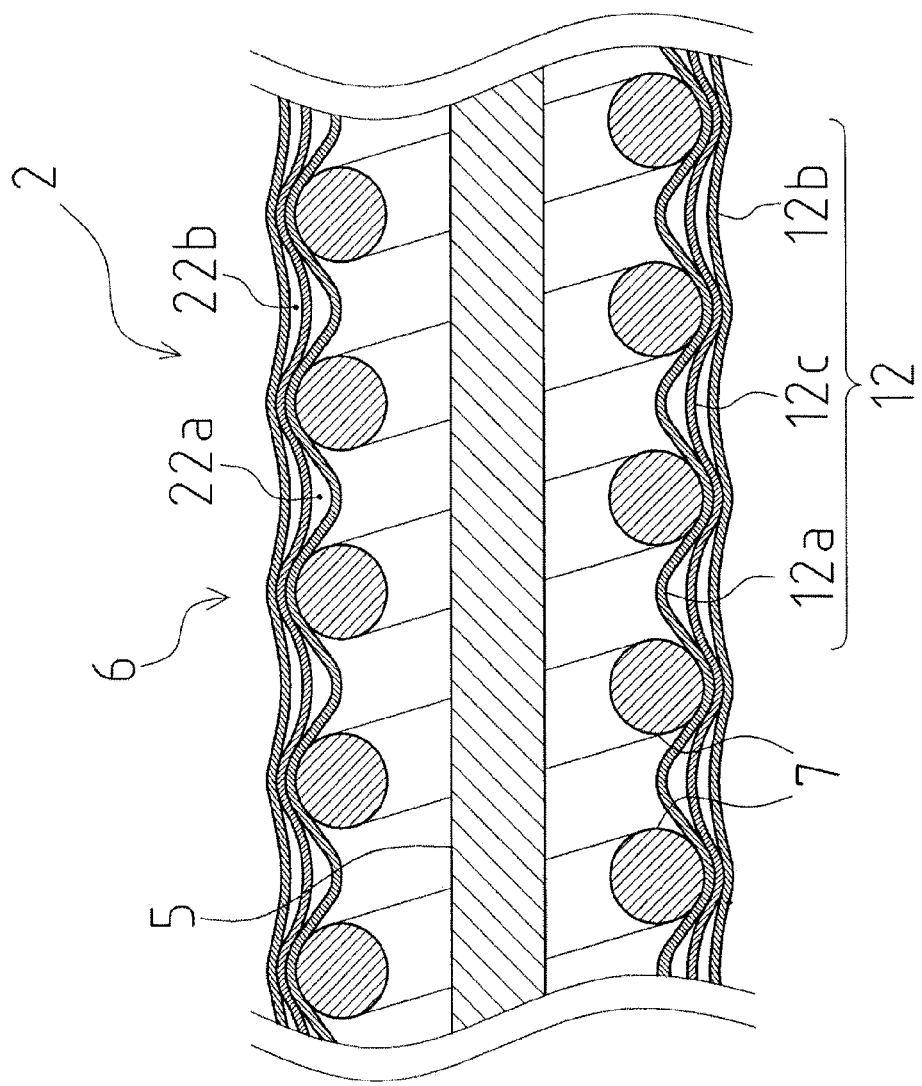
FIG. 3 is an enlarged view of a coil body and a coating portion of a guidewire according to an exemplary embodiment.

FIG. 3 is an enlarged view of the coil body 6 and a coating portion 12 of a guidewire 2. As illustrated in FIG. 3, the coating portion 12 that covers the coil body 6 includes three films (an inner film 12a, an intermediate film 12c, and an outer film 12b). Moreover, voids 22a are formed between portions of the inner film 12a that are arranged to come between the adjacent coils 7 of the coil body 6 and the intermediate film 12c, and voids 22b are formed between the intermediate film 12c and the outer film 12b.

In the guidewire 2, the core shaft 5 is inserted into the lumen of the coil body 6 similar to the guidewire 1.

In a guidewire 2, since the number of films constituting the coating portion 12 is larger than that of the guidewire 1, it is possible to improve the strength of the coating portion 12.

Moreover, since the voids 22a are formed between the inner film 12a and the intermediate film 12b and the voids 22b are formed between the intermediate film 12c and the outer film 12b, it is possible to sufficiently secure the bendability and the flexibility even when the number of films of the coating portion 12 is increased.

As described above, according to the guidewire 2, since the strength of the coating portion 12 can be improved while securing the bendability and the flexibility of the coating portion 12, it is possible to provide the guidewire 2 in which the coating portion 12 is rarely broken and the coil body 6 is easily bendable.

Figure 4:
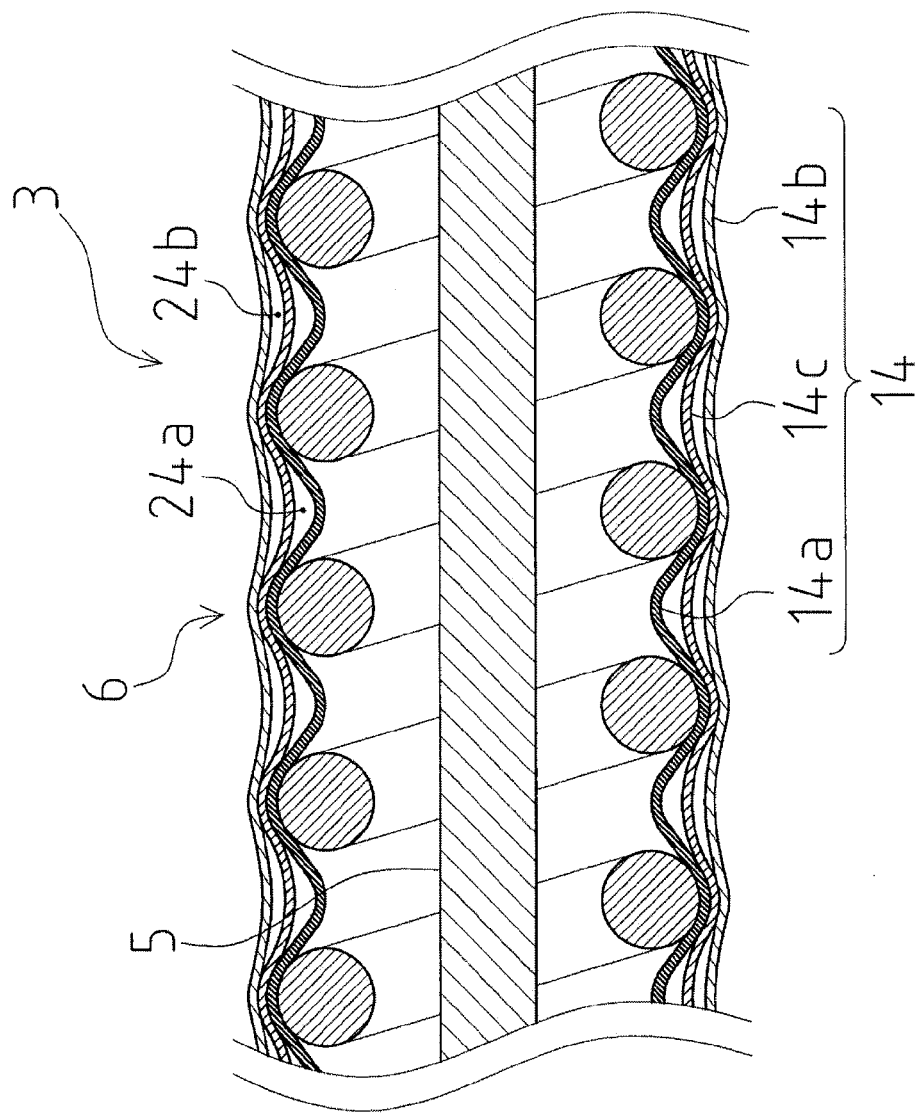
FIG. 4 is an enlarged view of a coil body and a coating portion of a guidewire according to an exemplary embodiment.

FIG. 4 is an enlarged view of the coil body 6 and a coating portion 14 of a guidewire 3. In FIG. 4, a difference in hatching density of the films (an inner film 14a, an intermediate film 14c, and an outer film 14b) constituting the coating portion 14 indicates a difference in the flexibility of the respective films. That is, a lightly hatched film has higher flexibility than a densely hatched film.

As illustrated in FIG. 4, the intermediate film 14c is more flexible than the inner film 14a, and the outer film 14b is more flexible than the intermediate film 14c.

The inner film 14a, the intermediate film 14c, and the outer film 14b are formed using different resins so that the respective films have different flexibility. However, the inner film 14a, the intermediate film 14c, and the outer film 14b may be formed using the same resin (for example, polyvinyl alcohol or the like) and the concentration of a cross-linker added to the resin may be adjusted so that the respective films have different flexibility. According to this method, it is possible to easily obtain a desired flexibility of a film.

Moreover, instead of forming the respective films of the coating portion 14 using different resins and adjusting the concentration of the cross-linkers of the respective films, the respective films may have different thicknesses (the intermediate film 14c may be thinner than the inner film 14a and the outer film 14b may be thinner than the intermediate film 14c). However, it is difficult to strictly control the thicknesses of the respective films of the coating portion 14. Thus, as described above, it may be easier to manufacture the guidewire 3 when the respective films are made to have different flexibility by using different resins and/or by adjusting the concentration of cross-linkers.

The other configurations of the guidewire 3 are the same as those of the guidewire 2. That is, the core shaft 5 is inserted into the lumen of the coil body 6. Moreover, voids 24a are formed between portions of the inner film 14a of the coating portions 14 that are arranged to come between the adjacent coils 7 of the coil body 6, and voids 24b are formed between the intermediate film 14c and the outer film 14b.

In the guidewire 3, similar to the guidewire 1 and the guidewire 2, voids 24a and 24b are formed between the plurality of films (the inner film 14a, the intermediate film 14c, and the outer film 14b) constituting the coating portion 14. Thus, it is possible to improve the bendability and flexibility of the coating portion 14 and to easily bend the coil body 6 (the guidewire 3).

Moreover, when the coil body 6 is curved, an outer film of the coating portion 14 is deformed more than an inner film. Thus, in the guidewire 3, by configuring the outer film that is deformed greatly when the coil body 6 is curved so as to be more flexible than the inner film, it is possible to make the coil body 6 curved more easily. As a result, it is possible to provide a guidewire having satisfactory followability even when the guidewire is inserted into a blood vessel that meanders complexly.

Although various embodiments of the guide wire have been described, the present invention is not limited to the embodiments but can be embodied in various forms without departing from the spirit thereof. For example, in the guidewires, voids are formed between the intermediate film and the outer film of the coating portion (see FIGS. 3 and 4). However, no void may be formed between the intermediate film and the outer film (the intermediate film may be closely attached to the outer film).

FIG. 5 is an enlarged view of the coil body 6 and a coating portion 16 of a guidewire 4. As illustrated in the drawing, in the guidewire 4, although voids 26 are formed between an inner film 16a and an intermediate film 16c of the coating portion 16, the intermediate film 16c is closely attached to an outer film 16b and no voids are formed between the outer and intermediate films.

In the guidewire 4, the core shaft 5 is inserted into the lumen of the coil body 6 similar to the guidewires described above.

In the guidewire 4, since the voids 26 are formed between the inner film 16a and the intermediate film 16c of the coating portion 16, it is possible to improve the bendability and flexibility of the coating portion 16 and to easily bend the coil body 6.

Moreover, since the intermediate film 16c is closely attached to the outer film 16b, it is possible to prevent the outer film 16b from peeling off of the intermediate film 16c.

Moreover, in the guidewires described above, the coating portion includes two or three films (see FIGS. 2 to 5). However, the coating portion may include four or more films (not illustrated).

However, if the coating portion includes too many films, it may become disadvantageous from the perspective of the bendability and flexibility of the coating portion. Thus, as in the above-described embodiments, the coating portion preferably includes two or three films.

Moreover, in the guidewires described above, the coil body is formed in such a shape that adjacent coils are not in contact with each other (loose winding). However, the coil body may be formed in such a shape that adjacent coils are in contact with each other (dense winding, not illustrated).

However, when the coil body is formed in a loose winding, it is possible to increase the size of the voids. As a result, it is possible to sufficiently secure the bendability and flexibility of the coating portion. Thus, the coil body is preferably formed in a loose winding as in the guidewires of the above-described embodiments.

What is claimed is:

1. A guidewire comprising:
   a core shaft;
   a coil body that has a plurality of coils and that covers the core shaft; and
   a coating portion that covers the coil body, the coating portion including a plurality of films that are stacked on each other, the plurality of films including an inner film and a second film,
   wherein:
     the inner film is disposed between adjacent coils of the plurality of coils, and
     the inner film and the second film are bent toward the core shaft between adjacent coils such that voids are formed between the inner film and the second film.

2. The guidewire according to claim 1, wherein:
   the plurality of films further includes an outer film,
   the second film is an intermediate film that is disposed between the inner film and the outer film, and
   the intermediate film and the outer film are separated such that voids are formed between the intermediate film and the outer film.

3. The guidewire according to claim 1, wherein:
   the plurality of films further includes an outer film,
   the second film is disposed between the inner film and the outer film,
   the second film and the outer film are separated such that voids are formed between the second film and the outer film, and
   the voids between the inner film and the second film and the voids between the second film and the outer film are located at axial locations of the guidewire corresponding to portions of the inner film that are disposed between the adjacent coils.

4. The guidewire according to claim 1, wherein the second film is more flexible than the inner film.

5. The guidewire according to claim 1, wherein the coating portion is hydrophilic.

6. The guidewire according to claim 1, wherein the inner film extends over less than an entire outer surface of each coil of the plurality of coils.

7. The guidewire according to claim 1, wherein the inner film extends over a portion of an outer surface of each coil of the plurality of coils.

8. The guidewire according to claim 1, wherein the voids extend at least partially between the adjacent coils of the plurality of coils.

9. The guidewire according to claim 3, wherein the voids between the inner film and the second film and the voids between the second film and the outer film extend at least partially between the adjacent coils of the plurality of coils.

* * * * *